United States Patent
Eaton

[19]

[11] Patent Number: 6,156,065
[45] Date of Patent: Dec. 5, 2000

[54] NATURAL FIXATION OF BREAST PROSTHESIS

[75] Inventor: L. Daniel Eaton, Little Rock, Ark.

[73] Assignee: Board of Trustees of the University of Arkansas, Little Rock, Ark.

[21] Appl. No.: 09/366,139

[22] Filed: Aug. 2, 1999

Related U.S. Application Data

[63] Continuation of application No. 08/926,906, Sep. 10, 1997, abandoned.

[51] Int. Cl.$^7$ ...................................................... A61F 2/52
[52] U.S. Cl. ................................... 623/7; 450/55; 450/54
[58] Field of Search .............................. 623/7, 8; 450/54, 450/55

[56] References Cited

U.S. PATENT DOCUMENTS

| | | |
|---|---|---|
| 2,580,264 | 12/1951 | Wright et al. . |
| 3,203,424 | 8/1965 | Garutso . |
| 3,255,754 | 6/1966 | Brumberger . |
| 3,498,297 | 3/1970 | Lord ........................................... 623/7 |
| 3,513,852 | 5/1970 | Seidl . |
| 3,641,592 | 2/1972 | Den Bleyker . |
| 3,651,522 | 3/1972 | Bernfeld . |
| 3,701,168 | 10/1972 | Balow . |
| 3,710,800 | 1/1973 | Carey . |
| 3,845,507 | 11/1974 | Kirby et al. . |
| 3,950,792 | 4/1976 | Williams . |
| 3,952,752 | 4/1976 | Huttle, Jr. . |
| 4,024,876 | 5/1977 | Penrock . |
| 4,086,666 | 5/1978 | Vaskys et al. . |
| 4,100,621 | 7/1978 | Ettipio . |
| 4,185,332 | 1/1980 | Jahnig . |
| 4,222,387 | 9/1980 | Têtu . |
| 4,245,644 | 1/1981 | Evans . |
| 4,364,880 | 12/1982 | Howse . |
| 4,369,792 | 1/1983 | Miller . |
| 4,378,805 | 4/1983 | Reichert et al. . |
| 4,401,492 | 8/1983 | Pfrommer . |
| 4,574,780 | 3/1986 | Manders . |
| 4,600,551 | 7/1986 | Erb . |
| 4,630,610 | 12/1986 | Fletcher . |
| 4,637,398 | 1/1987 | Sherwood ............................... 128/478 |
| 4,671,255 | 6/1987 | Dubrul et al. . |
| 4,676,795 | 6/1987 | Grundei . |
| 4,681,587 | 7/1987 | Eberl et al. . |
| 4,699,144 | 10/1987 | Sherwood ................................. 450/54 |
| 4,826,501 | 5/1989 | Grundei . |
| 4,841,992 | 6/1989 | Sasaki et al. . |
| 4,899,764 | 2/1990 | Gauger et al. . |
| 5,005,591 | 4/1991 | Austad . |
| 5,035,249 | 7/1991 | Sasaki et al. . |
| 5,035,758 | 7/1991 | Degler et al. . |
| 5,066,302 | 11/1991 | Rice . |

(List continued on next page.)

FOREIGN PATENT DOCUMENTS

| | | |
|---|---|---|
| 392960 | 10/1990 | European Pat. Off. . |
| 4115428 | 11/1992 | Germany . |
| 2202745 | 10/1988 | United Kingdom . |

*Primary Examiner*—David H. Willse
*Assistant Examiner*—Suzette J. Jackson
*Attorney, Agent, or Firm*—Ray F. Cox, Jr.

[57] ABSTRACT

A mastectomy garment for retaining a breast prosthesis in place on the anterior chest wall of a mastectomy patient. A combination bandeau/bra includes a normal bra cup for the natural breast (unless the patient has undergone a double mastectomy, in which case no normal bra cup is required), and a fold down cup for the prosthesis. Beneath the fold down cup a bandeau conforms to the anatomy of the patient's chest and presents a surface of hook and loop fastening material for the attachment of the breast prosthesis which carries mating hook and loop material on the posterior side. In one embodiment, the bandeau over the mastectomy site is provided with fenestration to improve the breathability of the site. The hook and loop fastening material on the bandeau covers substantially the entire portion of the bandeau over the mastectomy site allowing flexibility in the placement of the breast prosthesis on the bandeau. The fold down cup over the breast prosthesis is desirably held in position by a plurality of snap fasteners and by one or more tabs with hook and loop fastening material.

10 Claims, 2 Drawing Sheets

U.S. PATENT DOCUMENTS

| | | |
|---|---|---|
| 5,071,433 | 12/1991 | Naestoft et al. . |
| 5,098,330 | 3/1992 | Greenberg . |
| 5,116,370 | 5/1992 | Foglietti . |
| 5,133,752 | 7/1992 | Mandelkern . |
| 5,133,753 | 7/1992 | Bark et al. . |
| 5,158,541 | 10/1992 | McCurley . |
| 5,215,494 | 6/1993 | Flanagan . |
| 5,244,432 | 9/1993 | Moy Au et al. . |
| 5,352,307 | 10/1994 | Wild . |
| 5,376,323 | 12/1994 | Eaton . |
| 5,380,238 | 1/1995 | Crew-Gee . |
| 5,492,501 | 2/1996 | Brown ........................................ 450/31 |
| 5,527,359 | 6/1996 | Nakamura et al. . |
| 5,607,473 | 3/1997 | Weber-Unger et al. . |
| 5,700,288 | 12/1997 | Eaton . |
| 5,855,606 | 1/1999 | Eaton . |
| 6,074,420 | 6/2000 | Eaton ........................................... 623/7 |

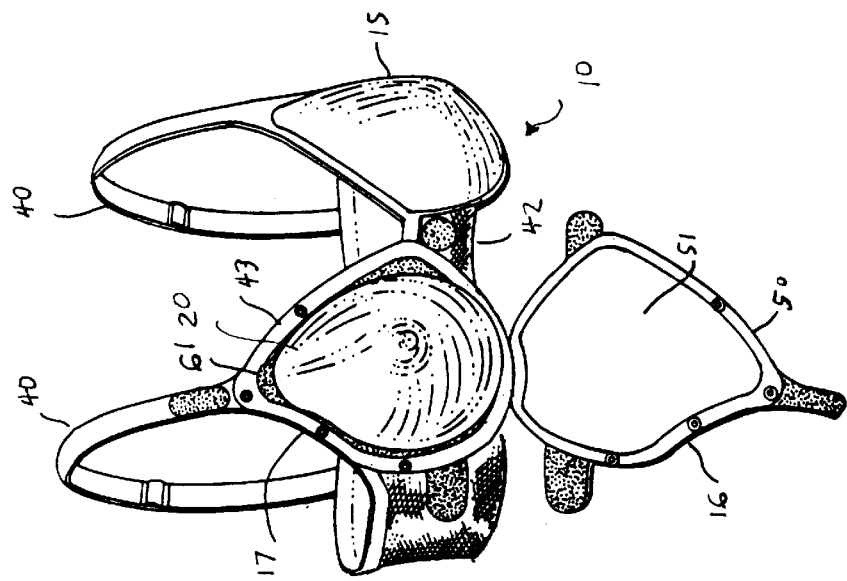
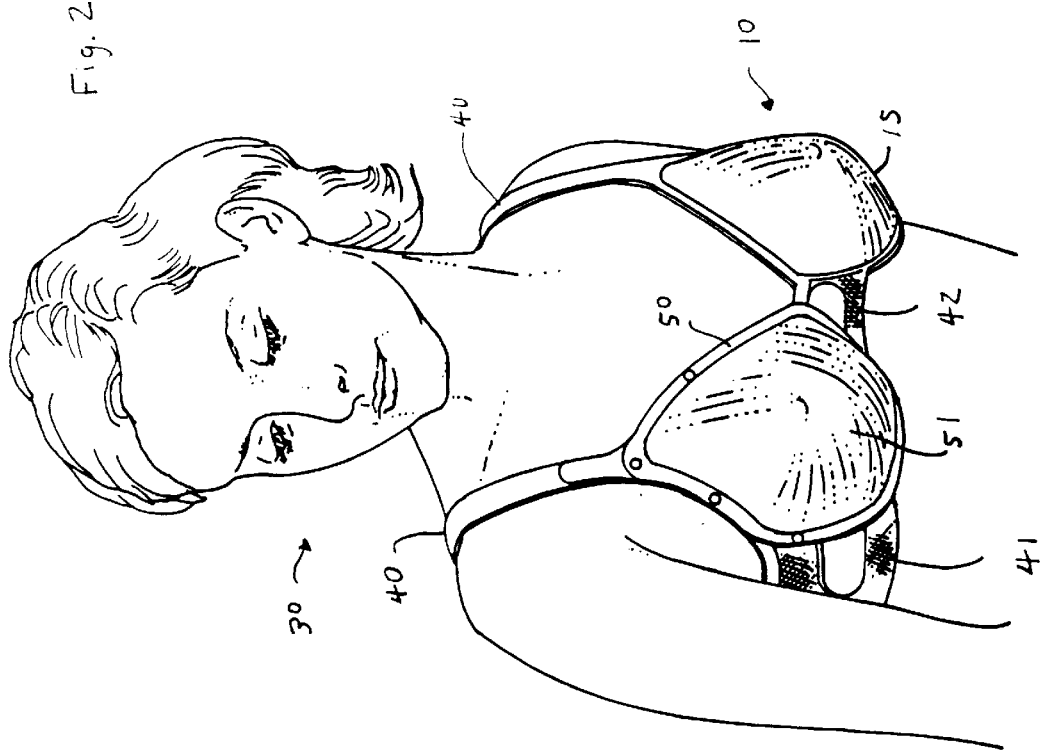

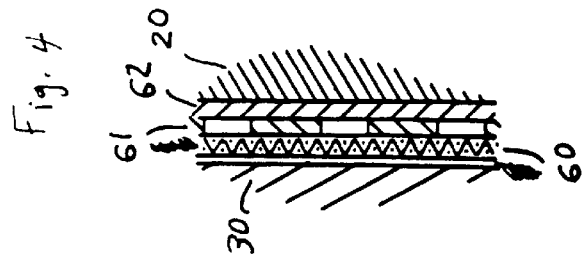
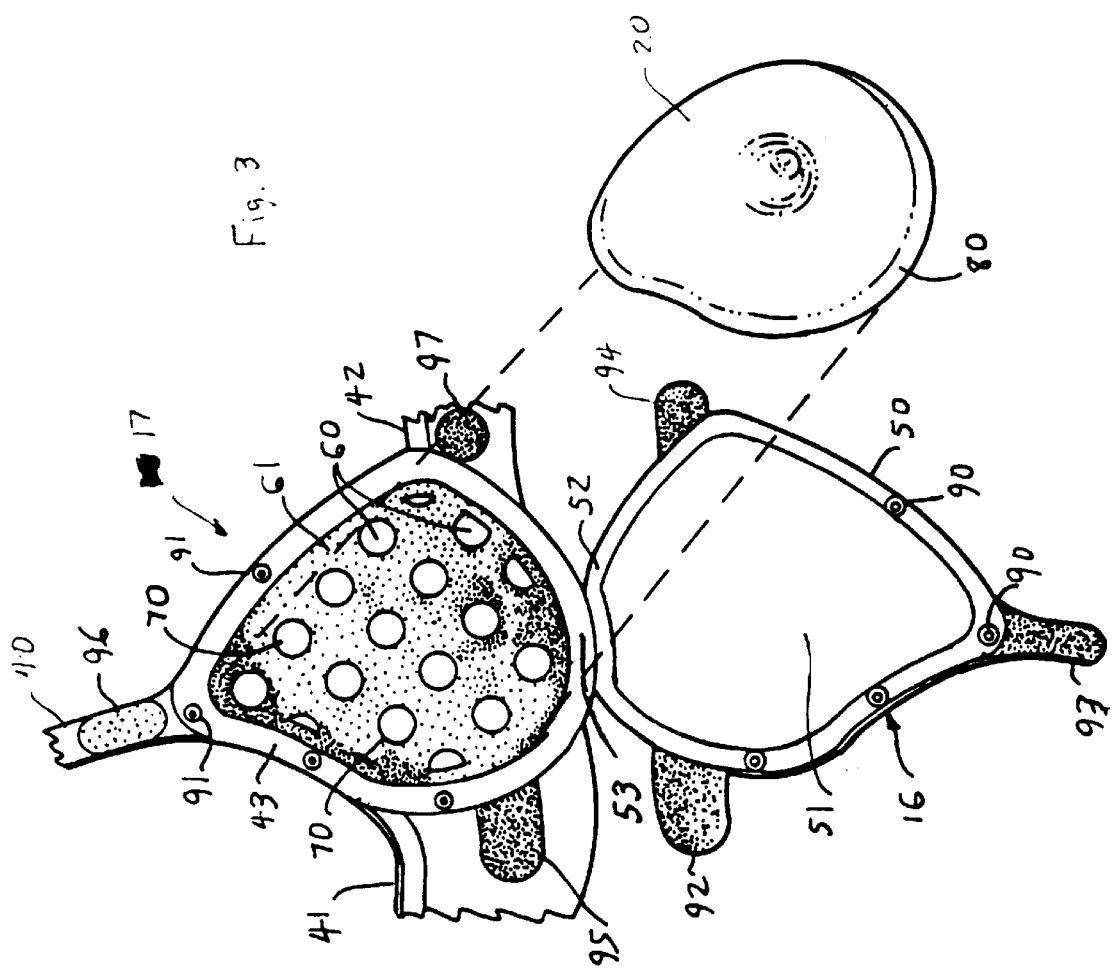

NATURAL FIXATION OF BREAST PROSTHESIS

This application is a continuation of copending application number 08/926,906 filed on Sept. 10, 1997 ABN.

BACKGROUND OF THE INVENTION

The present invention relates to a breast prosthesis garment for the secure fixation of a breast prosthesis, and particularly to a breast prosthesis garment in which the breast cup for the natural breast is replaced over the mastectomy site by a bandeau with hook and loop type fastening material for the fixation of the breast prosthesis and a folding cup for covering the breast prosthesis. In one embodiment the bandeau is fenestrated for improved air flow and thus greater comfort for the wearer.

Breast prostheses are necessary for women who have undergone radical mastectomies. An acceptable breast prosthesis should replicate the appearance of the natural breast while being comfortable to wear. The prior art of breast prostheses shows a number of attempts to achieve one or the other of these objectives, although with limited success at achieving both. Among the problems not completely solved in the prior art include achieving a natural look and feel to the prosthesis. Related to this problem is the perceived need to maintain a balanced weight of the prosthesis vis-a-vis the remaining natural breast. This may in fact be less of a problem with actual wearers who are likely to feel that weight is less of a concern than maintaining a natural relationship between the prosthesis and the chest of the wearer. Many patients complain that the location of the prosthesis in relation to the chest wall shifts and there is nothing in the way of "feedback" to the wearer that the prosthesis is in the correct position. An additional problem not well addressed by the prior art is the method of attachment or wearing of the breast prosthesis by the patient. One common solution is to attach the prosthesis directly to the chest of the patient with adhesives. This is obviously an uncomfortable solution and not always effective. Furthermore, a tight adhesive fit to the chest traps heat and prevents ventilation of the skin surface. Another common answer is to place the prosthesis in a pocket of a bra. This is also not a complete answer as the prosthesis may shift out of position within the bra, and, even if securely placed in the bra, does not have a natural feel to the wearer since it does not maintain its position with respect to the chest as is true of a natural breast.

Various attempts have been made to provides a breast prosthesis garment using two bras, and underbra to provide the prosthesis fixation and an outerbra for appearance. An example is U.S. Pat. No. 4,637.398 to Sherwood. Sherwood '398 discloses a mastectomy garment including an underbra, a breast prosthesis, and an outerbra. The underbra is of a form fitting material such as spandex. The underbra has attachment means, such as a ring of velcro material, for fixing the breast prosthesis to the underbra over the mastectomy site. An outerbra is described as a conventional off the shelf type of bra which is placed over the underbra and breast prosthesis and secured to the underbra to prevent relative movement. Sherwood '398 employs two layers of garments, including two layers of material over the site of the natural breast Sherwood '398 suggests attaching the breast prosthesis with a ring of velcro material which limits the ability of the user to position the prosthesis.

Somewhat related is U.S. Pat. No. 4,699,144, also to Sherwood. Sherwood '144 discloses a mastectomy garment including an underbra, a breast prosthesis, and an outerbra. As with Sherwood '398, the underbra and outerbra are secured one to the other to form a unitary garment. The breast prosthesis is placed in a pocket formed between the underbra and the outerbra and the pocket is then closed.

U.S. Pat. No. 5,071,433 issued to Naestoft et al. discloses the conventional technology employing adhesive attachment of hook and loop type material to the chest of the patient. The breast prosthesis may then be attached by mating hook and loop material on the posterior of the breast prosthesis.

Mandelkern discloses a prosthetic device formed of layers of materials. In one embodiment, the device is attached to the clothing of the user with hook, and loop type material.

U.S. Pat. No. 4,100,621 to Ettipio discloses a breast prosthesis having hook type fasteners at a plurality of locations around the periphery of the prosthesis for attachment to mating loop attachments on the inside of a nightgown.

U.S. Pat. No. 4,185,332 to Jahning discloses a breast prosthesis holder which comprises a pair of fabric panels over the area of the mastectomy site which constitute a pocket for holding the breast prosthesis. The pocket is closed with hook and loop type material.

U.S. Pat. No. 4,024,876 to Penrock discloses a fairly convention type of mastectomy bra with pockets with fold down panels for holding the prosthesis. Spring means hold the pockets closed after the breast prosthesis is placed within.

There are also a number of patents related to breast prostheses in general; for example, U.S. Pat. Nos. 3,845, 507; 4,826,501; and 5,066,302; in methods of forming breast prostheses; for example, U.S. Pat. Nos. 4,364,880; 4,600, 551; 4,401,492 5,035,758; and 5,352,307; and in bras for use in conjunction with breast prostheses; for example, U.S. Pat. Nos. 4,024,876; 4,369,792; 4,637,398; and 4,699,144. These patents are likewise considered relevant to the general state of the art.

The problems and disadvantages of the prior art are overcome by the present invention as described below.

SUMMARY OF THE INVENTION

The present invention is a device for retaining a breast prosthesis. in place on the anterior chest wall of a mastectomy patient. In the prior art, hook and loop type fastening material of the "velcro" type has been used to fix a breast prosthesis, but it is necessary to attach the velcro material to the skin of the patient with adhesive. The present invention by contrast carries one part of the hook and loop fastening material on a combination bandeau/bra which eliminates the difficulty and discomfort of the adhesive attachment. In contrast to a bra or similar garment which incorporates means to support or give a desired contour to the breast, the bandeau, as the term is used herein, is a band that conforms substantially to the chest wall. The combination bandeau/bra is designed with a normal bra cup for the natural breast (unless the patient has undergone a double mastectomy, in which case no normal bra cup is required), and a fold down cup for the prosthesis. Beneath the fold down cup the bandeau conforms to the anatomy of the patient's chest and presents a surface of hook and loop fastening material for the attachment of the breast prosthesis which carries mating hook and loop material on the posterior side.

The portion of the bandeau over the mastectomy site is preferably of a cotton material for breathability. Further, the preferred form of breast prosthesis as described in U.S. Pat.

Application Ser. No. 081683,816, incorporated herein by reference, has a concavity on the posterior side to provide an air space for comfort. In one embodiment of the invention, the bandeau over the mastectomy site may be provided with fenestration to improve the breathability of the site.

Since the hook and loop fastening material on the bandeau covers the entire portion of the bandeau over the mastectomy site, there is some flexibility, in the placement of the breast prosthesis on the bandeau. This is an advantage over the prior art in that the prior art normally allows the breast prosthesis to be attached in one position only.

The fold down cup over the breast prosthesis is desirably held in position by a plurality of snap fasteners and by one or more tabs with hook and loop fastening material.

The breast prosthesis is preferably made using the technique disclosed in U.S. Pat. No. 5,376,323, the disclosure of which is incorporated herein by reference, as described more fully below. The breast prosthesis is advantageously formed to match the remaining natural breast in shape, skin tint, etc.

The breast prosthesis may be custom made for a particular patient or may be of a standard type. In the latter case, a range of sizes and shapes may be employed to assure a compatible version for each individual patient. Using the technique of U.S. Pat. No. 5,376,323, the breast prosthesis is formed.

A mold is taken of the patient's torso to ensure the proper shape for the posterior side of the breast prosthesis. The anterior of the breast prosthesis may be a mirror image of the patient's remaining natural breast produced by techniques well known in the art or a standard mold may be used to produce this shape of the anterior of the prosthetic breast. The shape of the chest side of the breast prosthesis is preferably concave as is known in the art to avoid direct contact with the skin which inhibits proper ventilation of the skin surface. It should be understood that the present invention is not limited to breast prostheses made in this manner however. Breast prostheses manufactured by other techniques may be readily employed in the practice of the present invention.

It is therefore an object of the present invention to provide for a combined bandeau/bra which securely fixes a breast prosthesis,.

It is a further object of the present invention to provide for a breast prosthesis fixation device which allows full trunk and arm movement while retaining the breast prosthesis in position on the chest of the wearer.

It is an additional object of the present invention to provide for a combined bandeau/bra and breast prosthesis which allows flexible positioning of the breast prosthesis with respect to the chest of the wearer.

It is a still further object of the present invention to provide for a breast prosthesis fixation device which is comfortable and lightweight in fabrication and does not require irritating adhesive attachment to the skin.

These and other objects and advantages of the present invention will be apparent from a consideration of the following detailed description of the preferred embodiments in conjunction with the drawings which are briefly described as follows:

BRIEF DESCRIPTION OF THE DRAWINGS

FIG. 1 is a perspective view of the combination bandeau/bra of the present invention showing a breast prosthesis affixed to the bandeau portion of the invention and the prosthesis cup unfolded.

FIG. 2 is a perspective view of a mastectomy patient wearing the bandeau/bra of the present invention with the prosthesis cup folded.

FIG. 3 is a fragmentary perspective view of the bandeau portion of the present invention with the prosthesis cup unfolded and the breast prosthesis in exploded view. Also illustrated is an alternative embodiment of the present invention in which the bandeau is fenestrated for breathability.

FIG. 4 is a partial sectional side elevation view through the bandeau and breast prosthesis.

DETAILED DESCRIPTION OF THE PREFERRED EMBODIMENTS

The preferred embodiment of the present invention may be described with reference to FIGS. 1–3.

The present invention is a combined bandeau/bra 10 for retaining a breast prosthesis 20 in place on the anterior chest wall over the mastectomy site of a mastectomy patient 30 who has had one or both breasts removed. The description that follows will initially describe application of the present invention to the particular case of a single mastectomy, while embodiments for double mastectomies will be described following the initial description.

In contrast to a bra or similar garment which incorporates means to support or give a desired contour to the breast, a bandeau, as these term is used herein, is a band that conforms substantially to the chest wall. The present invention combines the a bandeau with a bra to produce a combination bandeau/bra 10 which has a conventional bra cup 15 for the natural breast (unless the patient has undergone a double mastectomy, in which case no conventional bra cup 15 is required), and a fold-down prosthesis cup 16 for the breast prosthesis 20. Beneath the fold-down prosthesis cup 16 the bandeau 17 conforms to the anatomy of the patient's chest. The bandeau 17 and the bra cup 15 are attached together with a center strap 42 in the vicinity of the patient's sternum and are provided with the conventional complement of shoulder straps 40, side straps 41 and fasteners to form a complete garment in the nature of a conventional bra. While a particular arrangement of straps is described herein, such description is not intended to limit the present invention which may be practiced with any variation of such straps and fasteners as would be well known to those of skill in the art. Such straps may desirably be of elastic material.

The bandeau 17 is defined by a edge strap 43 which is desirably of elastic material and serves to hold the bandeau 17 taut over the mastectomy site so as to conform comfortably to the anterior chest wall of the patient 30 over the mastectomy site. The edge strap 43 encircles the mastectomy site.

The fold-down prosthesis cup 16 comprises an edge portion 50 and a prosthesis-covering portion 51. The prosthesis-covering portion may be of any suitable material supporting the breast prosthesis 20, but desirably the prosthesis-covering portion is compatible in appearance with the bra cup 15 over the natural breast so as to present an overall appearance, when worn by the patient with a breast prosthesis, virtually indistinguishable from a conventional bra.

The fold-down prosthesis cup 16 is attached along a lower edge 52 of the edge portion 50 to the bottom portion 53 of the edge strap 43 of the bandeau 17 by a foldable attachment. Such foldable attachment may be by a sewn seam, by manufacturing the edge strap 43 of the bandeau 17 and the edge portion 50 of the prosthesis cup 16 from a single piece of material, or by any other means known to those skilled in the art.

While the bra cup 15 and straps 40, 41, 42 may be fabricated of any suitable material of the type employed in conventional bras, it is desirable that the material of the bandeau touching the skin of the patient be of cotton or similar material for comfort and breathability. Such material is able to conform to the patient's anterior chest wall, provide firm support for the breast prosthesis, and is breathable to allow trapped heat and moisture from the mastectomy site to escape.

The construction of the bandeau 17 is described with reference to FIG. 4. As described above, the material closest to the chest wall of the patient 30 is a inner layer 60 which is preferably of cotton. On top of the inner layer 60 is a loop material 61. The loop material 61 may, for example, be of loop type fastening material of the type produced under the name "velcro." Alternatively, the loop material 61 may be of any other type of material which would serve the same function; i.e., as a fastener which removably attaches to hook type fastening material. In one embodiment the loop material 61 covers substantially all of the inner layer 60. However, material which has a "pile" or similar texture suitable for the practice of the present invention may also be heavy and heat insulating in effect when placed near the skin. To overcome this problem, an alternative embodiment of the loop material 61 is shown is FIG. 3. In the alternative embodiment the loop material 61 is provided with a plurality of fenestrations 70 which are openings exposing the underlying inner 'layer 60. This effectively increases the permeability of the bandeau to heat and moisture and prevents heat and moisture from being trapped next to the skin of the patient. In either embodiment of the loop material 61, the loop material 61 is effectively dispersed over the entire surface of the inner layer 60.

Furthermore, the preferred form of the breast prosthesis 20 is as described in U.S. patent application Ser. No. 08/683,816, incorporated herein by reference, which has a concavity on the posterior side to provide an air space for comfort. Thus only a rim 80 around the circumference of the breast prosthesis 20 actually contacts the bandeau 17.

Again with reference to FIG. 4, the rim 80 of the breast prosthesis 20 is provided with hook fastening material 62 which engages with loop material 61 to attach the breast prosthesis 20 to the bandeau 17. Hook fastening material 62 may be arrange in a ring shape to cover the entire posterior rim 80 of the breast prosthesis 20. However, this is not necessary and a plurality of patches of hook material arrayed around the rim 80 would be acceptable so long as a sufficient number of patches are placed at intervals along the rim 80 to provide firm overall attachment of the breast prosthesis 20. It is important to note that the superimposed layered thicknesses of the inner layer 60, the loop material 61, and the hook fastening material 62 space the rim 80 of the breast prosthesis 20 away from the skin of the patient 30, thus providing an air space around the rim 80 to improve breathability.

The combined bandeau/bra of the present invention is worn in the following fashion. The combined bandeau/bra is assumed by the wearer in the normal manner as for conventional bras. The fold-down cup 16 is placed in the fold down position as shown in FIGS. 1 and 3. The breast prosthesis 20 is placed into position on the bandeau 17 so that the hook fastening material 62 on the posterior side of the breast prosthesis 20 engages the loop material 61 on the bandeau 17. Since the breast prosthesis 20 is removably fastened to the bandeau 17, the breast prosthesis 20 may be removed and repositioned as often as necessary to achieve an acceptable feel and appearance. It is an important feature of the present invention that the loop material 61 covers substantially all of the bandeau 17 which in turn covers a large area over the mastectomy site. The wearer thus has a great amount of freedom to position the breast prosthesis 20 for optimum feel and appearance.

Once the breast prosthesis 20 is positioned to the satisfaction of the wearer, the fold-down prosthesis cup 16 is folded up and over the breast prosthesis 20. The prosthesis cup 16 thus provides support to the breast prosthesis 20 in the same manner as the cup of a conventional bra to a normal breast. The fold-down cup 16 is attached to the bandeau 17 by a plurality of snap fasteners 90 arrayed along the edge portion 50 of the prosthesis cup 16 which fasten to a plurality of complementary fasteners 91 arrayed in complementary locations along the edge strap 43. Additional security and comfort may be obtained by providing hook-and-loop type fasteners along the shoulder strap 40, center strap 42 and side strap 41. For example, hook tabs 92, 93, 94 mate with loop tabs 95, 96, 97, respectively, located respectively along the side strap 41, shoulder strap 40 and center strap 42.

The preceding description assumes the practice of the present invention with respect to a patient who has suffered a single mastectomy. However, the present invention may be practiced with a double mastectomy simply by eliminating the breast cup 15 and substituting a second bandeau 17.

The present invention has been described with reference to certain preferred and alternative embodiments which are intended to be exemplary only and not limiting to the full scope of the present invention as set forth in the appended claims.

What is claimed is:

1. In combination, a breast prosthesis and a mastectomy garment for supporting a natural breast and the breast prosthesis over the mastectomy site on a mastectomy patient, comprising:

a mastectomy garment comprising a combined bandeau and bra having a cup for supporting the natural breast and a bandeau portion over the mastectomy site and conforming substantially to the chest of the mastectomy patient over the mastectomy site;

said bandeau portion having hook and loop fastening material on the anterior of said bandeau portion, said hook and loop fastening material covering substantially all said bandeau portion;

a breast prosthesis having mating hook and loop fastening material on the posterior side of said breast prosthesis whereby said breast prosthesis is removably attached to said bandeau portion and further whereby said breast prosthesis may be positioned horizontally, vertically and rotationally on said bandeau portion for optimal feel and appearance; and a prosthesis cup foldably attached to a lower edge of said bandeau portion for covering and supporting said breast prosthesis in a first folded up position and for access to said breast prosthesis in a second folded, down position;

said prosthesis cup further comprising means for removably fastening said prosthesis cup to said bandeau portion in said first folded up position.

2. The combination of claim 1 wherein said bandeau portion and said hook and loop fastening material of said bandeau portion further comprise one or more fenestrations for breathability.

3. The combination of claim 2 wherein said breast prosthesis further comprises a posterior concavity.

4. The combination of claim 3 wherein said means for removably fastening said prosthesis cup comprises a plurality of snap fasteners disposed on the periphery of said prosthesis cup and a plurality of mating snap fasteners on said bandeau portion.

5. The combination of claim 4 wherein said means for removably fastening said prosthesis cup further comprises at least one tab on said periphery of said prosthesis cup having hook and loop fastening material thereon and mating patches of hook and loop fastening material on said mastectomy garment.

6. In combination, a breast prosthesis and a mastectomy garment for supporting at least one breast prosthesis over a mastectomy site on a mastectomy patient, comprising:

a mastectomy garment comprising a bandeau having a bandeau portion over a mastectomy site and conforming substantially to the chest of the mastectomy patient over said mastectomy site;

said bandeau portion having hook and loop fastening material on the anterior of said bandeau portion, said hook and loop fastening material covering substantially all said bandeau portion;

a breast prosthesis having mating hook and loop fastening material on the posterior side of said breast prosthesis whereby said breast prosthesis is removably attached to said bandeau portion and further whereby said breast prosthesis may be positioned vertically, horizontally and rotationally on said bandeau portion for optimal feel and appearance; and a prosthesis cup foldably attached to a lower edge of said bandeau portion for covering and supporting said breast prosthesis in a first folded up position and for access to said breast prosthesis in a second folded down position;

said prosthesis cup further comprising means for removably fastening said prosthesis cup to said bandeau portion in said first folded up position.

7. The combination of claim 2 wherein said bandeau portion and said hook and loop fastening material of said bandeau portion further comprise one or more fenestrations for breathability.

8. The combination of claim 7 wherein said breast prosthesis further comprises a posterior concavity.

9. The combination of claim 8 wherein said means for removably fastening said prosthesis cup comprises a plurality of snap fasteners disposed on the periphery of said prosthesis cup and a plurality of mating snap fasteners on said bandeau portion.

10. The combination of claim 9 wherein said means for removably fastening said prosthesis cup further comprises at least one tab on said periphery of said prosthesis cup having hook and loop fastening material thereof and mating patches of hook and loop fastening material on said mastectomy garment.

* * * * *